US011607249B2

(12) United States Patent
Sonoda et al.

(10) Patent No.: US 11,607,249 B2
(45) Date of Patent: Mar. 21, 2023

(54) UTERINE MANIPULATOR ARRANGEMENT

(71) Applicant: MEMORIAL SLOAN KETTERING-CANCER CENTER, New York, NY (US)

(72) Inventors: Yukio Sonoda, New York, NY (US); Paul Booth, New York, NY (US); Jon Massucci, Eastchester, NY (US)

(73) Assignee: MEMORIAL SLOAN KETTERING-CANCER CENTER, New York, NY (US)

( * ) Notice: Subject to any disclaimer, the term of this patent is extended or adjusted under 35 U.S.C. 154(b) by 162 days.

(21) Appl. No.: 16/069,767

(22) PCT Filed: Jan. 13, 2017

(86) PCT No.: PCT/US2017/013365
§ 371 (c)(1),
(2) Date: Jul. 12, 2018

(87) PCT Pub. No.: WO2017/123891
PCT Pub. Date: Jul. 20, 2017

(65) Prior Publication Data
US 2019/0029723 A1  Jan. 31, 2019

Related U.S. Application Data

(60) Provisional application No. 62/278,149, filed on Jan. 13, 2016.

(51) Int. Cl.
*A61B 17/42* (2006.01)
*A61B 17/00* (2006.01)

(52) U.S. Cl.
CPC ............. *A61B 17/4241* (2013.01); *A61B 2017/00473* (2013.01); *A61B 2017/4216* (2013.01)

(58) Field of Classification Search
CPC ........ A61B 17/4241; A61B 2017/4216; A61B 2017/4225; A61B 17/282; A61B 2017/00477; A61B 2017/00473
See application file for complete search history.

(56) References Cited

U.S. PATENT DOCUMENTS 3,779,248 A   12/1973   Karman
3,926,192 A   12/1975   Van Maren
(Continued)

FOREIGN PATENT DOCUMENTS

CN   202843741   4/2013
CN   203315049   12/2013
(Continued)

OTHER PUBLICATIONS

Communication pursuant to Rule 164(1) EPC dated Aug. 21, 2019 for European patent application No. 17739015.0.
(Continued)

*Primary Examiner* — Thomas McEvoy
(74) *Attorney, Agent, or Firm* — Hunton Andrews Kurth LLP

(57) ABSTRACT

An exemplary apparatus, according to an exemplary embodiment of the present disclosure, can include, for example, a uterine manipulator having a clamp arrangement having a first tip(s) and a second tip(s), and a colpotomy ring arrangement coupled to the clamp arrangement on or at the first tip(s), and including an opening(s) in an outer surface thereof for insertion of the second tip(s) therethrough when the clamp arrangement is in a closed position. In some exemplary embodiments of the present disclosure, the clamp arrangement can include a uterine manipulator. The first tip(s) can include a plurality of removable tips, where each of the tips can have a different length from one another. In certain exemplary embodiments of the present disclosure, the first tip(s) can have a variable length.

22 Claims, 13 Drawing Sheets

(56) References Cited

U.S. PATENT DOCUMENTS

| | | | |
|---|---|---|---|
| 4,323,057 A * | 4/1982 | Jamieson | A61B 1/32 600/221 |
| 5,108,408 A | 4/1992 | Lally | |
| 5,697,937 A | 12/1997 | Toma | |
| 5,840,077 A | 11/1998 | Rowden et al. | |
| 2003/0009085 A1 * | 1/2003 | Arai | A61B 1/00089 600/127 |
| 2004/0158262 A1 | 8/2004 | Burbank et al. | |
| 2004/0236349 A1 * | 11/2004 | Gellman | A61B 17/42 606/119 |
| 2006/0184197 A1 * | 8/2006 | Shifrin | A61B 17/122 606/205 |
| 2007/0142860 A1 | 6/2007 | Kotmel et al. | |
| 2008/0188863 A1 | 8/2008 | Chu | |
| 2012/0109147 A1 | 5/2012 | Auerbach et al. | |
| 2015/0351621 A1 | 12/2015 | Hill et al. | |
| 2018/0256181 A1 * | 9/2018 | Bonadio | A61B 90/08 |

FOREIGN PATENT DOCUMENTS

| | | |
|---|---|---|
| DE | 102014008927 A1 | 12/2015 |
| WO | 2002065924 A2 | 8/2002 |
| WO | WO 2013/151512 | 10/2013 |

OTHER PUBLICATIONS

European Extended European Search report dated Dec. 3, 2019 for European application No. 17739015.0.

\* cited by examiner

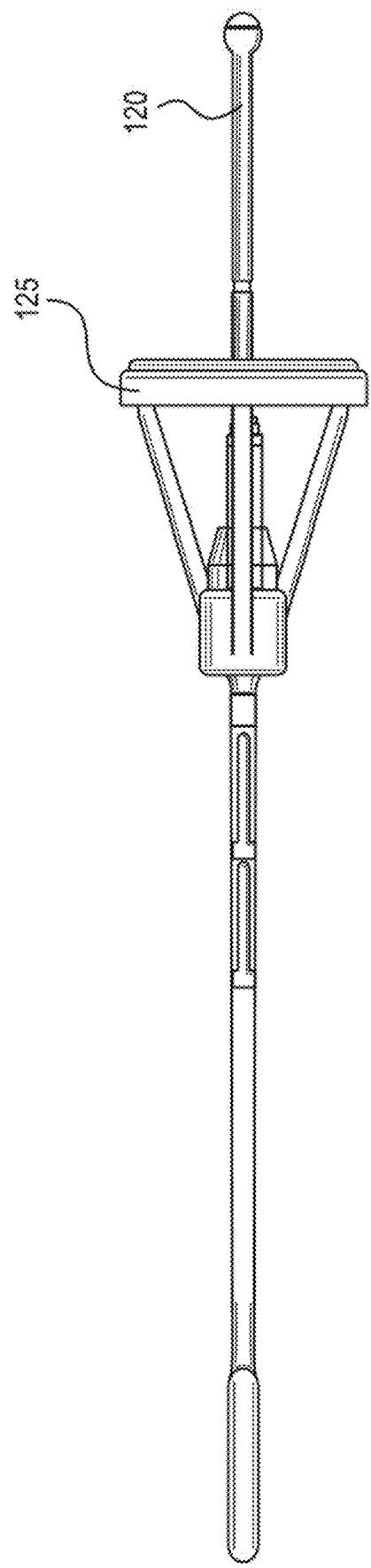

UTERINE MANIPULATOR ARRANGEMENT

CROSS-REFERENCE TO RELATED APPLICATION(S)

The present application relates to and claims priority from International Patent Application No. PCT/US2017/013365 filed on Jan. 13, 2917 and from U.S. Provisional Patent Application No. 62/278,149, filed on Jan. 13, 2016, the entire disclosure of which is incorporated herein by reference.

FIELD OF THE DISCLOSURE

The present disclosure relates generally to a medical device, and more specifically, to exemplary embodiments of an exemplary uterine manipulator.

BACKGROUND INFORMATION

Uterine manipulators are medical devices that are used to hold the uterus in place during surgery (e.g., during a hysterectomy). Current devices are made of plastic, are of inferior quality and often slip out during surgery, which can cause complications. For example, various uterine manipulators are available such as the Jarcho cannula or a tenaculum, both of which are essentially sponge sticks. There are also more complex manipulators available, such as the VCare® Uterine Manipulator/Elevator. However, uterine manipulators—in a stick form—have the disadvantage in that they can easily slip out. Currently-available devices are also complicated to use. For example, currently-available devices require two separate components (a colpotomy ring and a cannula) in order to perform the surgery. While such instruments may be capable when performing the specific task they are designed for, their drawbacks do not easily facilitate complex interactions often required between tool interactions in the uterine environment. The separate devices can be unwieldy to use, and can be difficult to place and maintain during surgery. Specifically, independently manipulating a separate colpotomy ring and a uterine cannula is non-optimal in a real world surgical setting.

Thus, it may be beneficial to provide an exemplary uterine manipulator arrangement, which can overcome at least some of the deficiencies described herein above.

SUMMARY OF EXEMPLARY EMBODIMENTS

An exemplary apparatus, according to an exemplary embodiment of the present disclosure, can include, for example, a uterine manipulator having a clamp arrangement having a first tip(s) and a second tip(s), and a colpotomy ring arrangement coupled to the clamp arrangement on or at the first tip(s), and including an opening(s) in an outer surface thereof for insertion of the second tip(s) therethrough when the clamp arrangement is in a closed position. In some exemplary embodiments of the present disclosure, the clamp arrangement can include a tenaculum manipulator. The first tip(s) can include a plurality of removable tips, where each of the tips can have a different length from one another. In certain exemplary embodiments of the present disclosure, the first tip(s) can have a variable length.

In some exemplary embodiments of the present disclosure, the first tip(s) can be coupled to the clamp arrangement using a key arrangement. The second tip(s) can include a hook tip, and the second tip(s) can be fixed to the clamp arrangement. A locking lug(s) can be configured to be inserted over the first tip(s) in order to secure the first tip(s) to the clamp arrangement. The colpotomy ring arrangement can be coupled to the clamp arrangement using the locking lug(s). In certain exemplary embodiments of the present disclosure, the colpotomy ring arrangement can include a ring shelf provided on the outer surface thereof or a groove provided on the outer surface thereof. In some exemplary embodiments of the present disclosure, the uterine manipulator can be configured to be inserted into a vagina of a patient.

Exemplary embodiments of the present disclosure can also include a colpotomy ring, which can include, for example, a first end configured to be coupled to a clamp arrangement, and a second end opposite the first end that can include a first circular portion and a second circular portion. The first circular portion can have a first outer surface that can have a first diameter and the second circular portion can have a second outer surface that can have a second diameter. The second diameter can be smaller than the first diameter.

Exemplary embodiments of the present disclosure can also include a colpotomy ring, which can include, for example, a first end configured to be coupled to a clamp arrangement, and a second end opposite the first end that can include a circular portion having a groove.

These and other objects, features and advantages of the exemplary embodiments of the present disclosure will become apparent upon reading the following detailed description of the exemplary embodiments of the present disclosure, when taken in conjunction with the appended claims.

BRIEF DESCRIPTION OF THE DRAWINGS

Further objects, features and advantages of the present disclosure will become apparent from the following detailed description taken in conjunction with the accompanying Figures showing illustrative embodiments of the present disclosure, in which:

FIG. 5 is an exemplary diagram showing a top-down view of the exemplary device from FIG. 1 according to an exemplary embodiment of the present disclosure;

Figure 1:
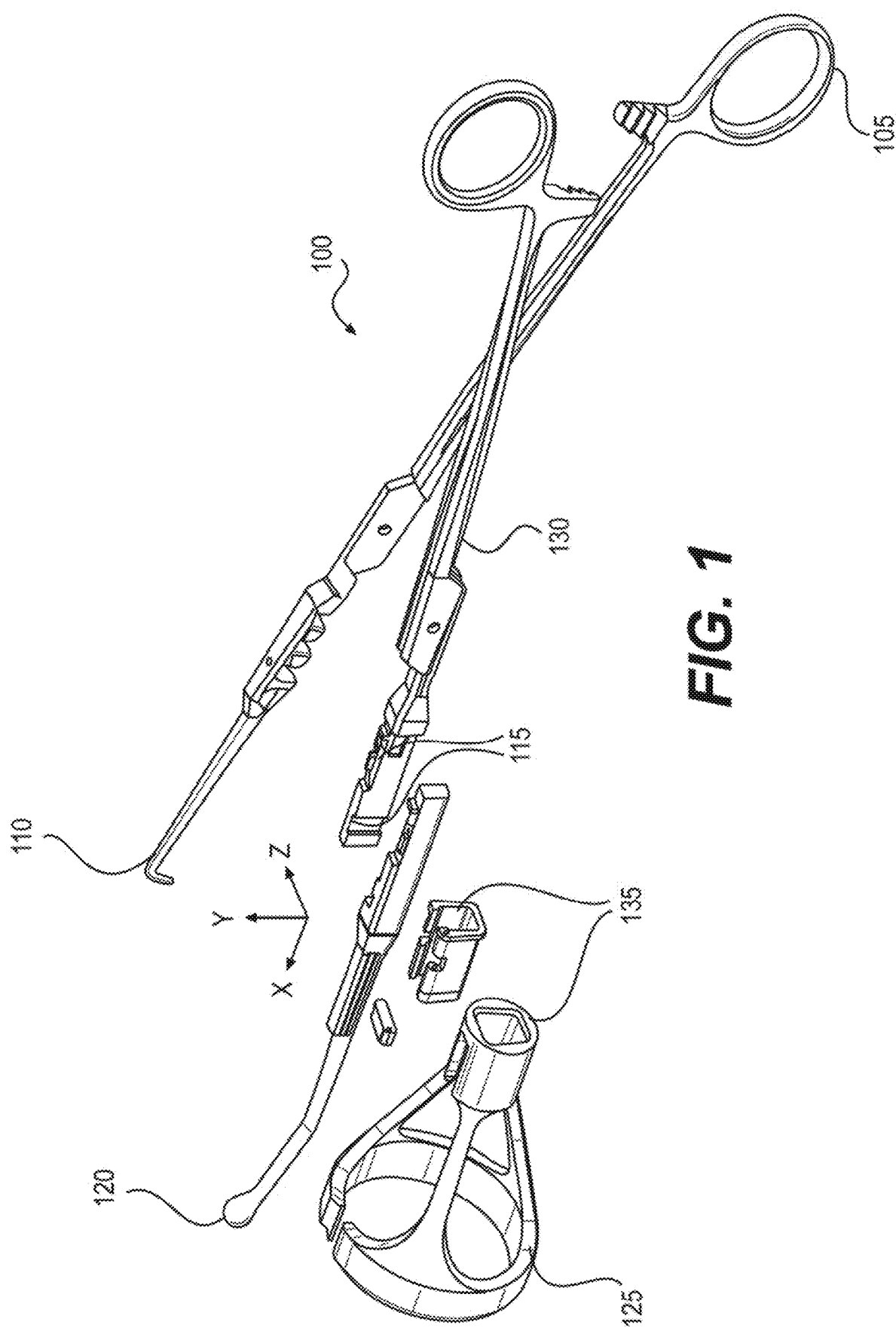
FIG. 1 is an exemplary diagram of an exploded view of an exemplary device extending in a first direction according to an exemplary embodiment of the present disclosure.

Throughout the drawings, the same reference numerals and characters, unless otherwise stated, are used to denote like features, elements, components or portions of the illustrated embodiments. Moreover, while the present disclosure will now be described in detail with reference to the figures, it is done so in connection with the illustrative embodiments and is not limited by the particular embodiments illustrated in the figures and the appended claims.

DETAILED DESCRIPTION OF EXEMPLARY EMBODIMENTS

According to an exemplary embodiment of the present disclosure, the exemplary device described herein can be used for performing laparoscopic and/or robotic hysterectomies. For example, the exemplary uterine manipulator arrangement can be a device that can facilitate laparoscopic and/or robotic hysterectomies. Placement of the exemplary device can be used to position the uterus in such a manner that the entire procedure can be easily performed. In contrast, current instruments that are used for the same procedure are unreliable (e.g., they are plastic, disposable and can slip out of the uterine cavity), and also can be difficult to place and to use. The exemplary device can combine a tenaculum clamp that can hold on to the cervix of the uterus, as well as a colpotomy ring that can aid in delineating the cervico-vaginal junction, to enable the hysterectomy to be performed. In an exemplary embodiment of the present disclosure, the colpotomy ring can be placed separately, and then attached to the clamp.

The exemplary device can integrate the utility of the tenaculum clamp and a colpotomy ring, while also being rigid. Various colpotomy ring sizes can be included, as well as various tip lengths. An exemplary pneumo-retaining balloon can be used to facilitate particular positioning of the exemplary device.

As shown in the diagrams of FIGS. 1-11C, an exemplary device or clamp 100 (e.g., including but not limited to a tenaculum clamp) can include a proximal end 105 and a distal end 110. The distal end 110 can include a mating surface 115 (e.g., a primary key and a secondary key for tip mating), which can be used to lock a tip 120 (e.g., a removable tip) in place (e.g., attached to the uterine manipulator). As shown in the diagrams of FIGS. 6A-6C, the removable tip 120 can vary in length (e.g., there can be multiple removable tips 605 and 610 each having its own length). Alternatively, or in addition, a single removable tip can be used that can have an adjustable length. Additionally, the tip 120 can be permanently attached to the distal end and can be adjustable in length. The tip 120 can be connected to the clamp 100 at location 615 using any suitable connection, including an interference fit as shown in the diagrams of FIGS. 6B and 6C.

Figure 2:
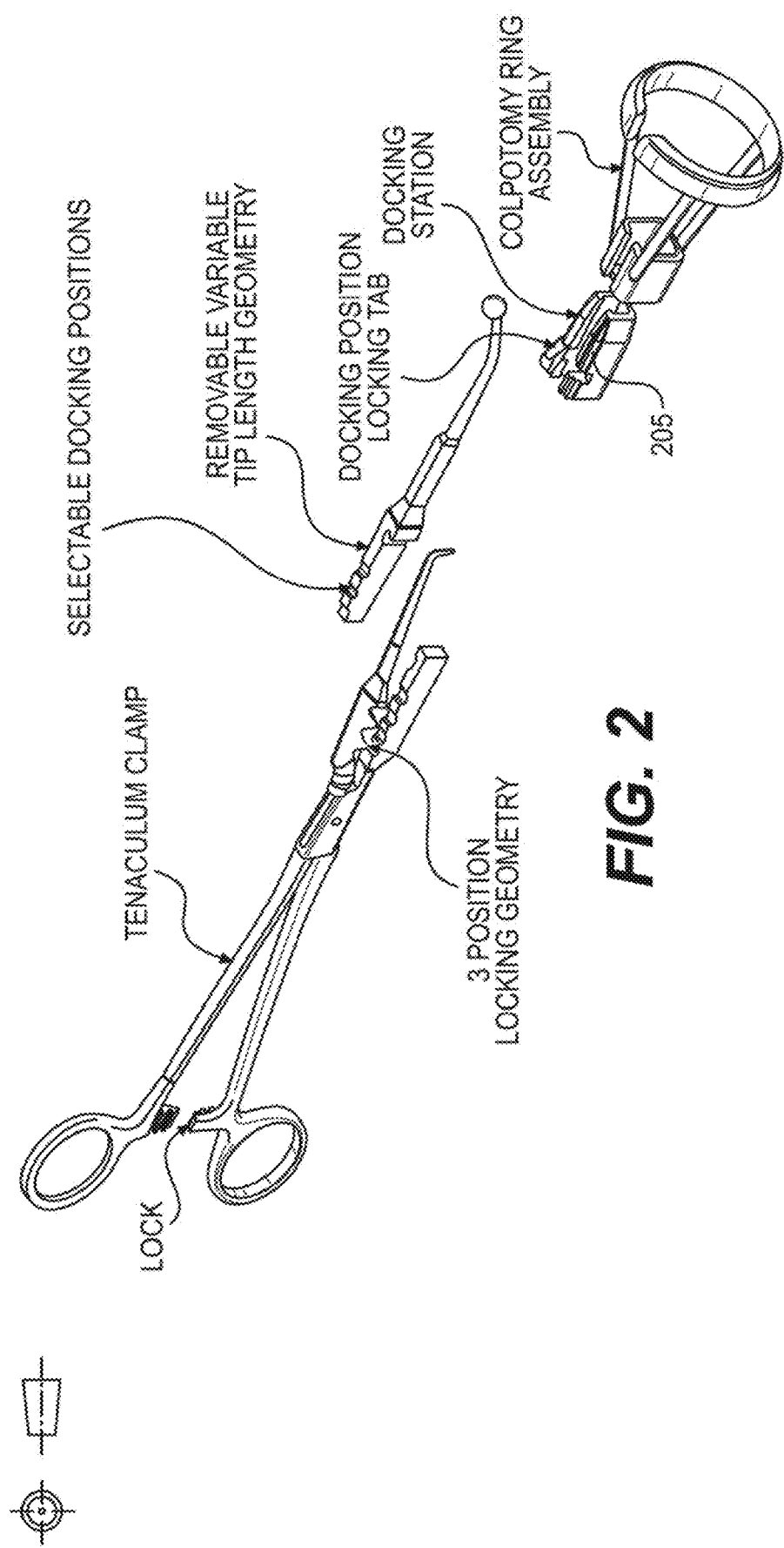
FIG. 2 is an exemplary diagram showing a perspective view of the exemplary device from FIG. 1 extending in a second direction according to an exemplary embodiment of the present.
Figure 3:
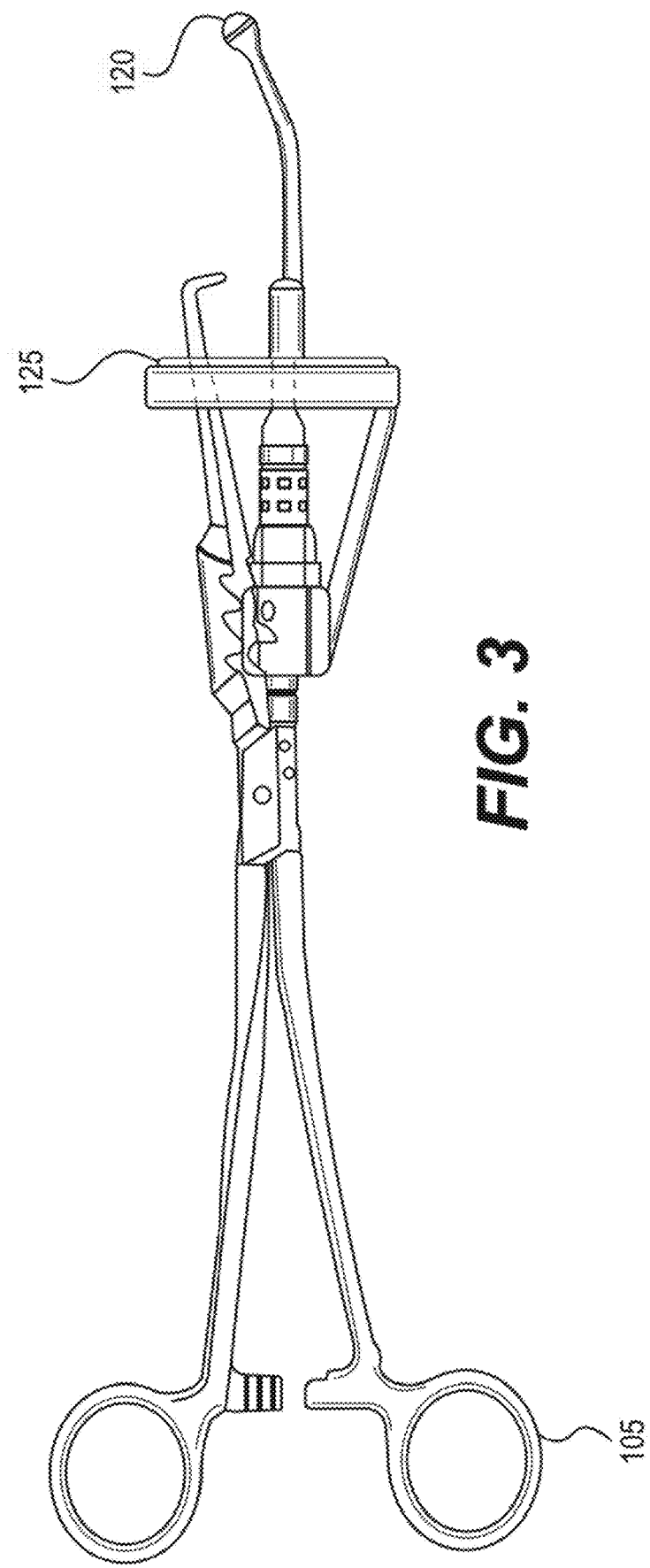
FIG. 3 is an exemplary diagram showing a side view of the exemplary device from FIG. 1 according to an exemplary embodiment of the present disclosure.
Figure 4:
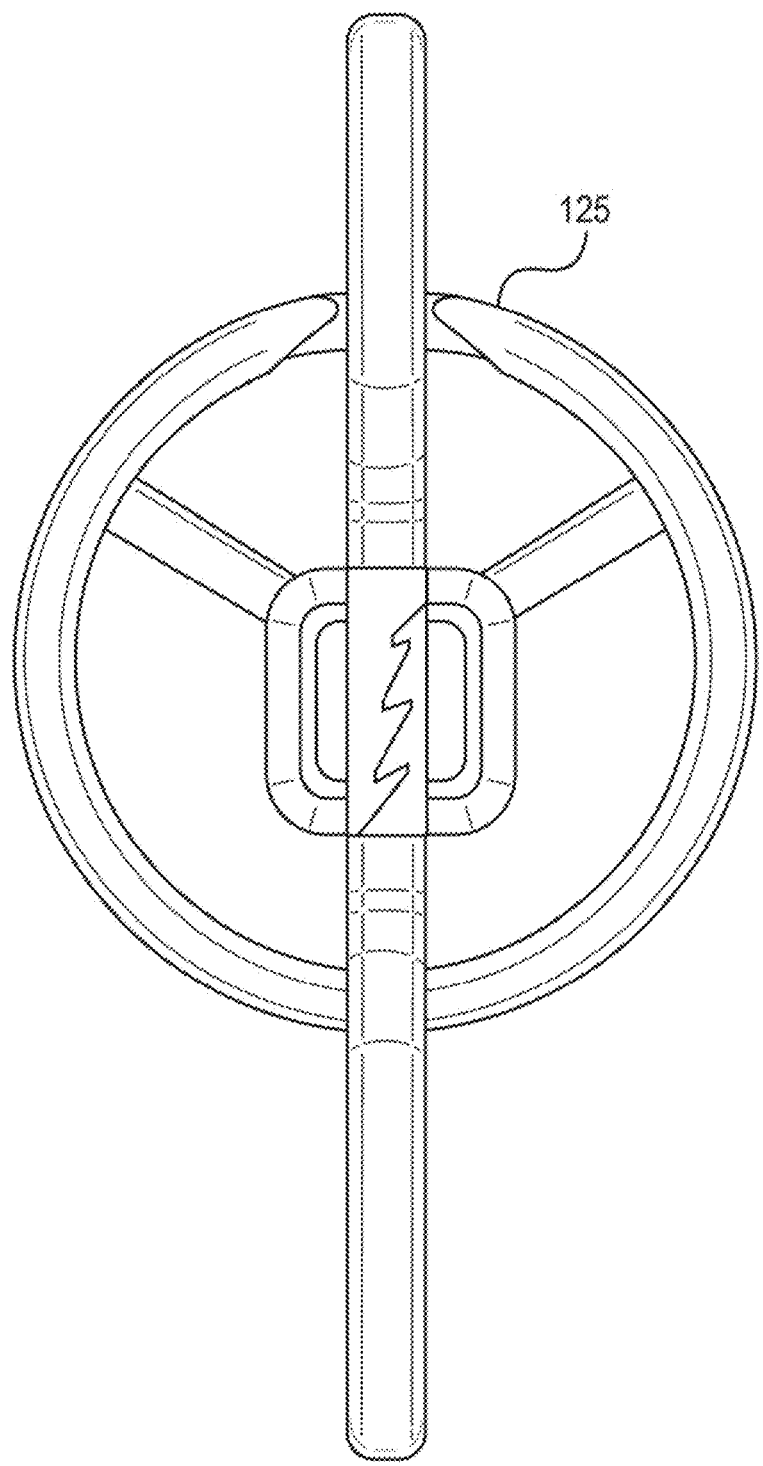
FIG. 4 is an exemplary diagram showing a front view of the exemplary device from FIG. 1 according to an exemplary embodiment of the present disclosure.
Figure 6A:
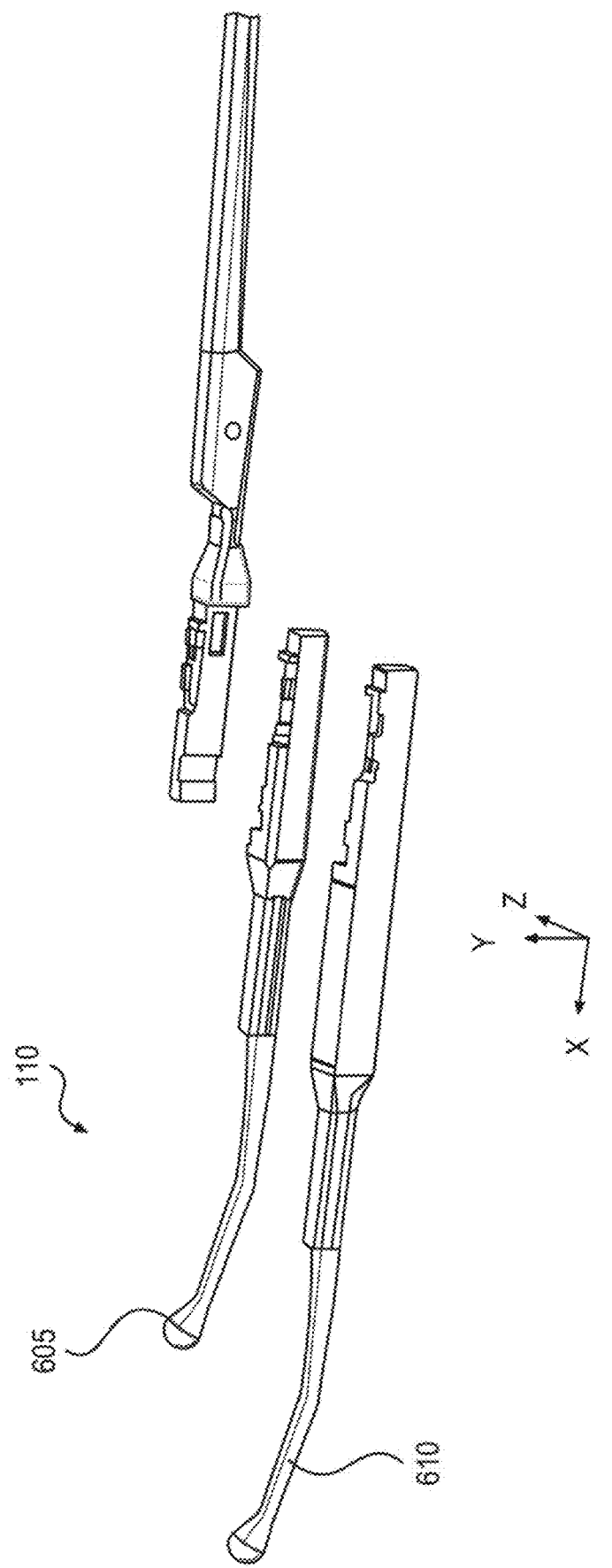
FIGS. 6A-6C are exemplary diagrams illustrating exemplary connection between the variable length tip and the clamp according to an exemplary embodiment of the present disclosure.
Figure 6B:
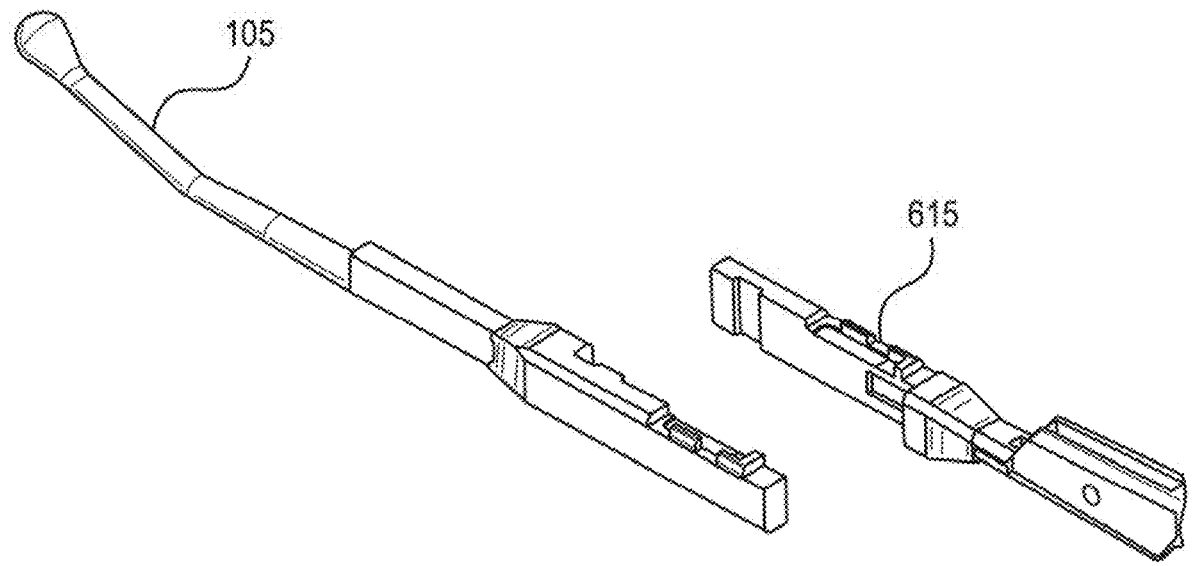
Figure 6C:
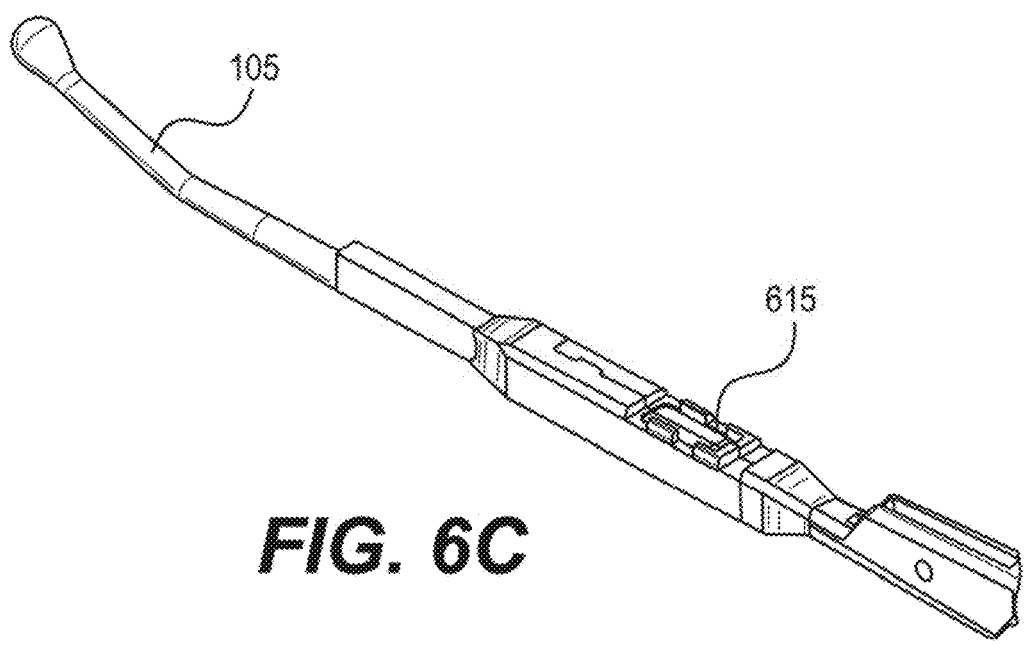

The variable length tips can facilitate positive locking of the colpotomy ring 125 to the handle 130 when the clamp 100 is shut, regardless of the position of the colpotomy ring 125. The removable tip 120 can be locked in one of a plurality of positions (e.g., 3 positions as shown in the diagram of FIG. 2), and it can be coupled to, and moved through, the colpotomy ring 125 assembly using a docking station that can have a docking position locking tab 205. The colpotomy ring 125 can include a lug 135 that can be keyed for single orientation fit and the exemplary colpotomy ring 125 can be formed from, or machined from, a single piece of material (e.g., from a single piece of metal such as stainless steel).

Figure 7A:
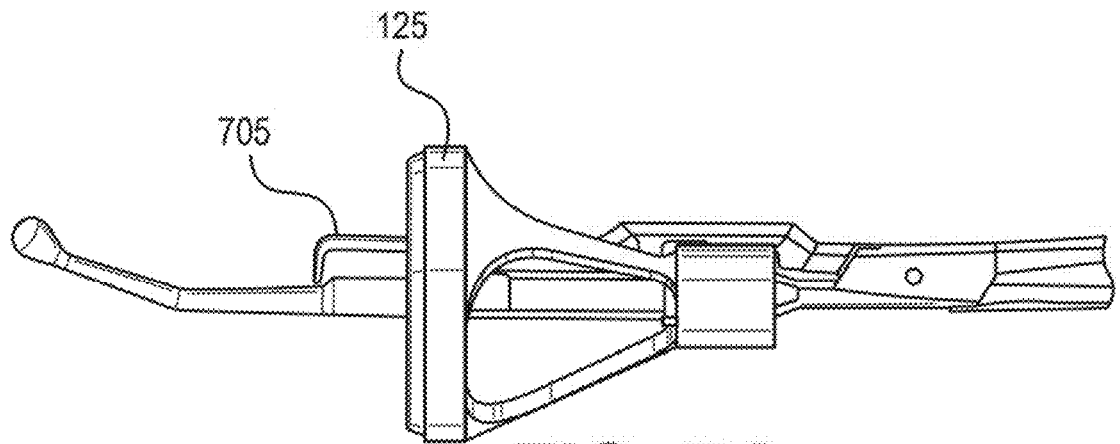
FIGS. 7A-7C are exemplary close-up diagrams of a distal end of the exemplary device from FIG. 1 according to an exemplary embodiment of the present disclosure.
Figure 7B:
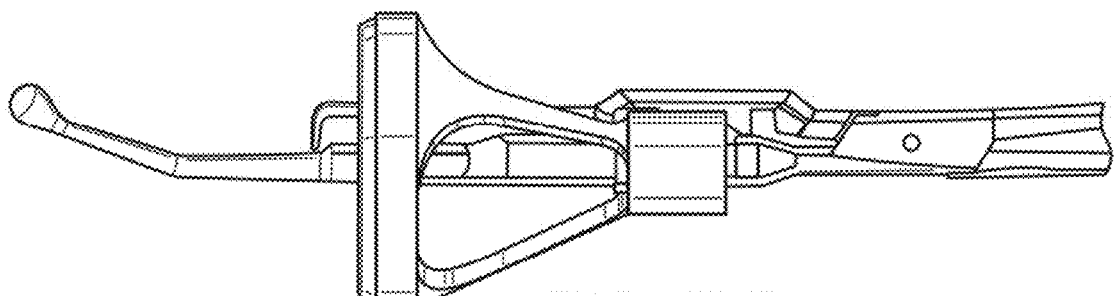
Figure 7C:
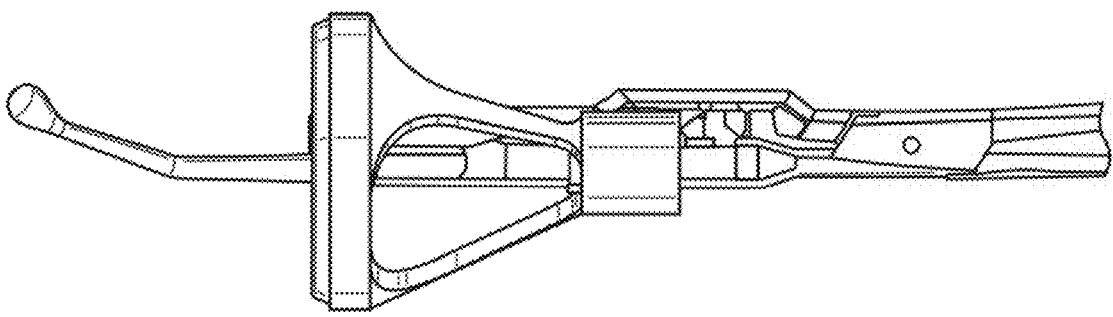
Figure 8A:
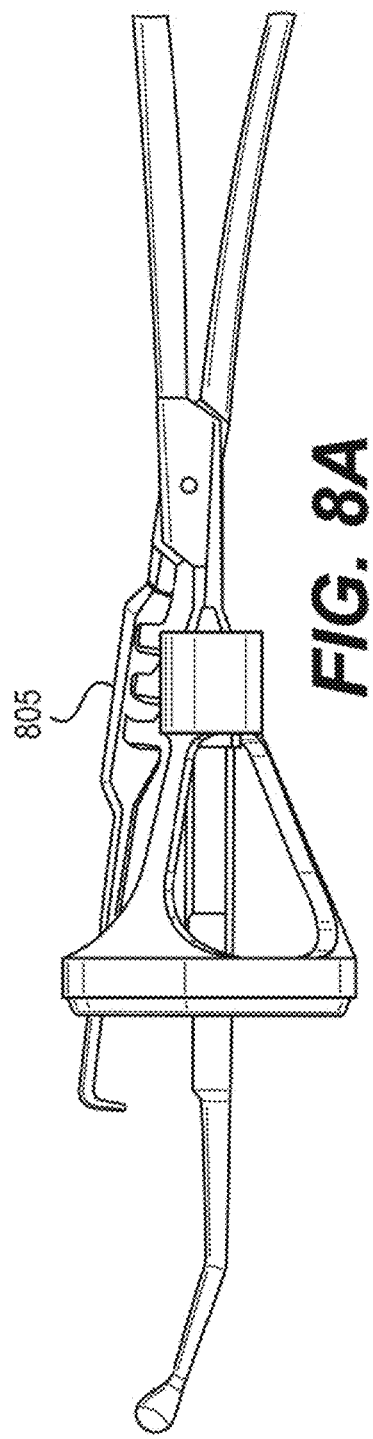
FIGS. 8A-8C are further exemplary close-up diagrams of the distal end of the exemplary device from FIG. 1 according to an exemplary embodiment of the present disclosure.
Figure 8B:
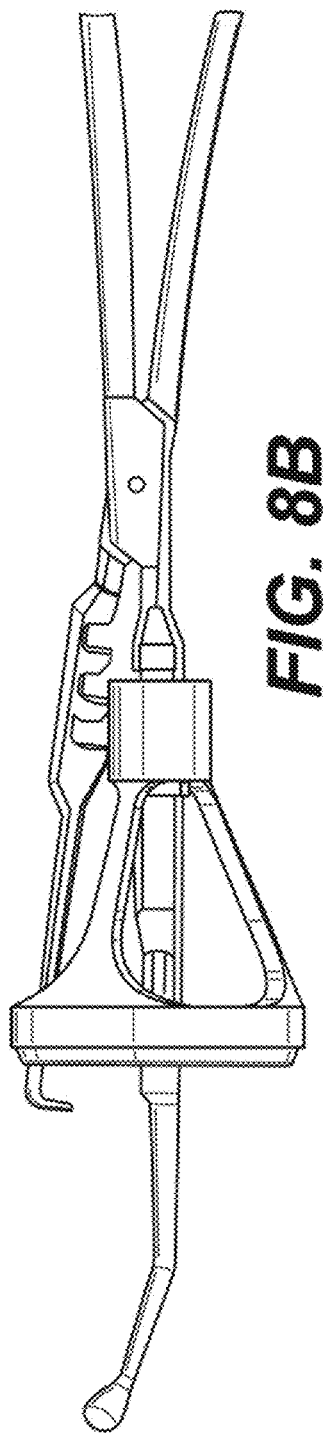
Figure 8C:
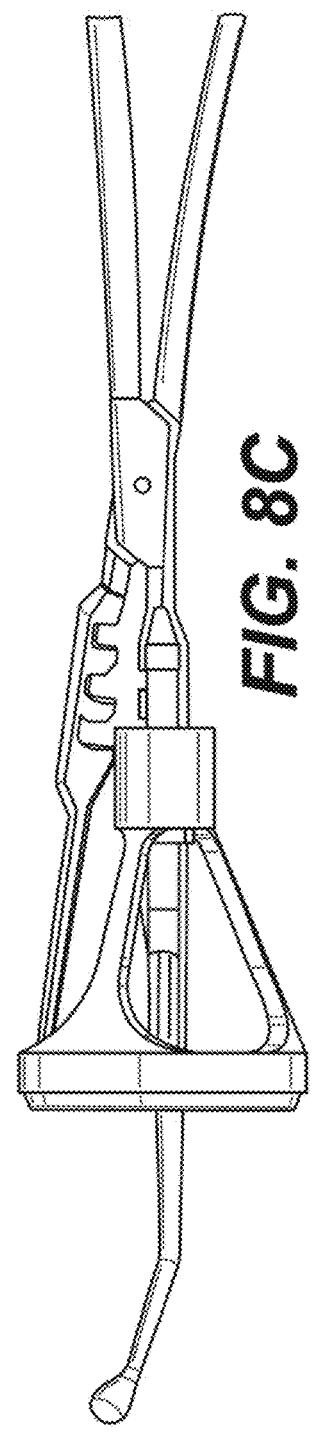

As shown in the diagram of FIG. 1, the locking lug 135 can be used to further lock the variable length tip 120 to the clamp 100. This can facilitate the prevention of the variable length tip 120 from detaching during use. As shown in FIGS. 7A-7C, the colpotomy ring 125 can be placed in a plurality of positions (e.g., three positions as shown, although not limited thereto), and the placement of the colpotomy ring 125 can be dependent on the length of the tip 120 chosen and/or on the locking lug 135, although not limited thereto. For example, the colpotomy ring 125 can be placed in a first position that facilitates the hook tip of the tenaculum clamp 705 to extend a particular amount (e.g., distance) out of the colpotomy ring 125. (See, e.g., diagram shown in FIG. 7A). Various other positions for the colpotomy ring 125 can be selected, which can affect the distance that hook tip of the tenaculum clamp 705 extends from the colpotomy ring 125. (See, e.g., diagram shown in FIG. 7B). At a particular position of the colpotomy ring 125 (see, e.g., diagram shown FIG. 7C), the hook tip of the tenaculum clamp 705 may not extend at all past the colpotomy ring.

In some exemplary embodiments of the present disclosure, the distance between the hook tip of the tenaculum clamp 705 and the variable length tip 120 can be selected and/or changed, for example, based on the patient. Alternatively, the exemplary device can be configured such that the distance between the hook tip of the tenaculum clamp 705 and the variable length tip 120 can be approximately constant (e.g., about 0.5 cm, about 1 cm, about 2 cm, about 3 cm, etc.) regardless of the position that the colpotomy ring 125 is locked in. (See, e.g., diagrams shown in FIGS. 8A-8C). This can be accomplished, for example, using variable-length teeth 805 provided on the clamp, which can affect the height of the locking lug 135 with respect to the clamp.

Figure 9A:
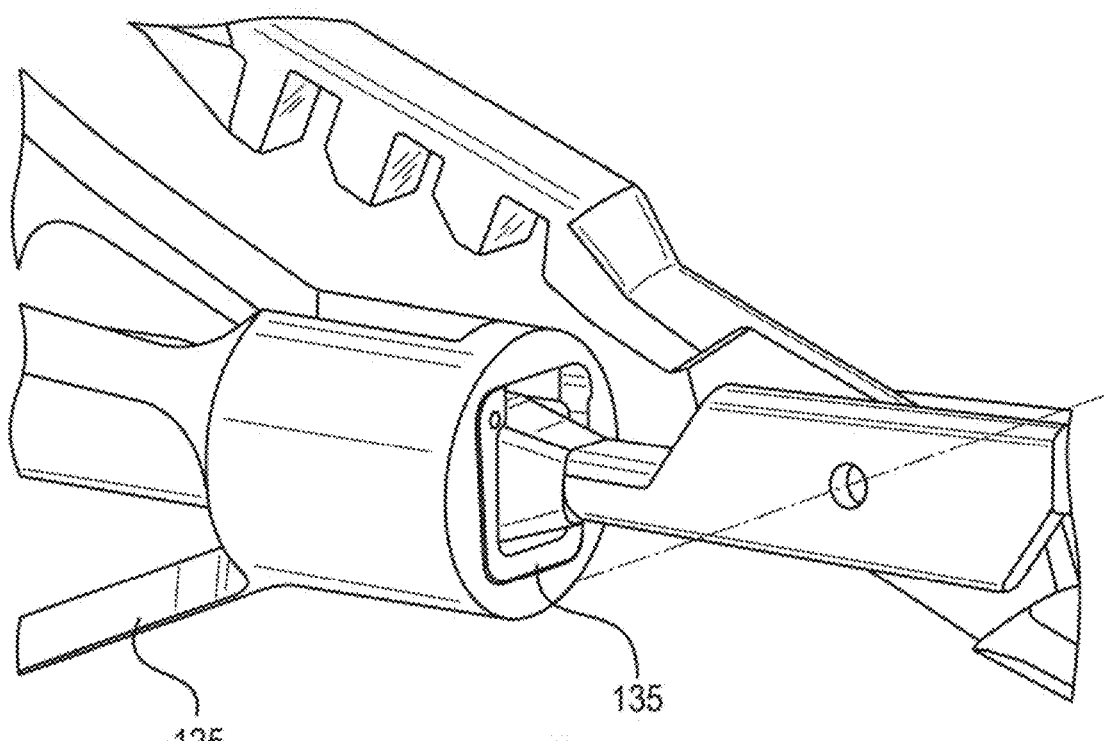
FIG. 9A is an exemplary close-up diagram of the colpotomy ring placed over the locking lug with the tenaculum clamp in the open position according to an exemplary embodiment of the present disclosure.
Figure 9B:
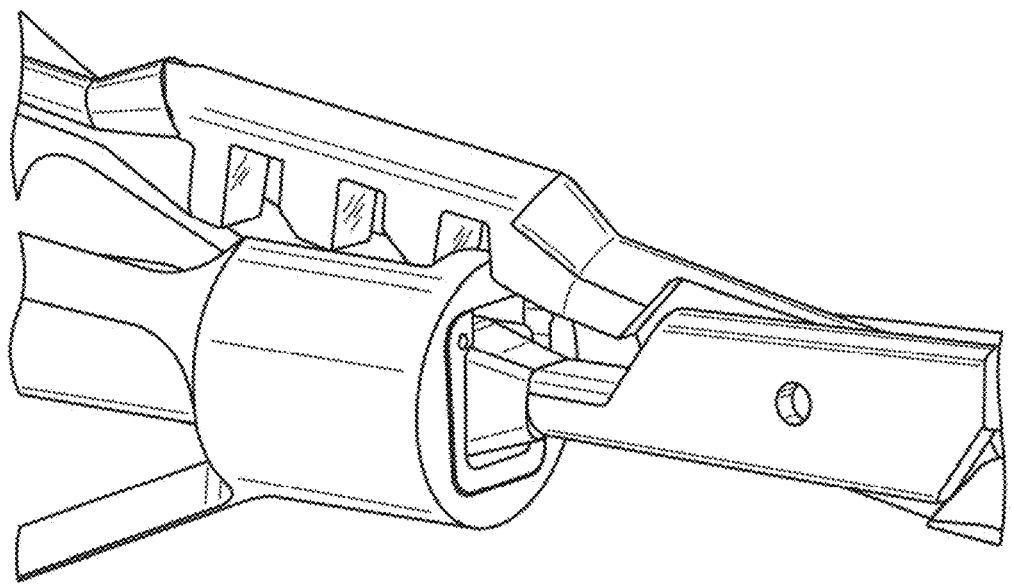
FIG. 9B is an exemplary close-up diagram of the colpotomy ring placed over the locking lug with the tenaculum clamp in the closed position according to an exemplary embodiment of the present disclosure.

As shown in the diagrams of FIGS. 9A and 9B, the colpotomy ring 125 can then be placed over the locking lug 135, while the clamp 100 is in the open position (see, e.g., diagram shown FIG. 9A), and the colpotomy ring 125 can be locked in place when the clamp 100 is in the closed position. (See, e.g., diagram shown FIG. 9B).

Figure 10:
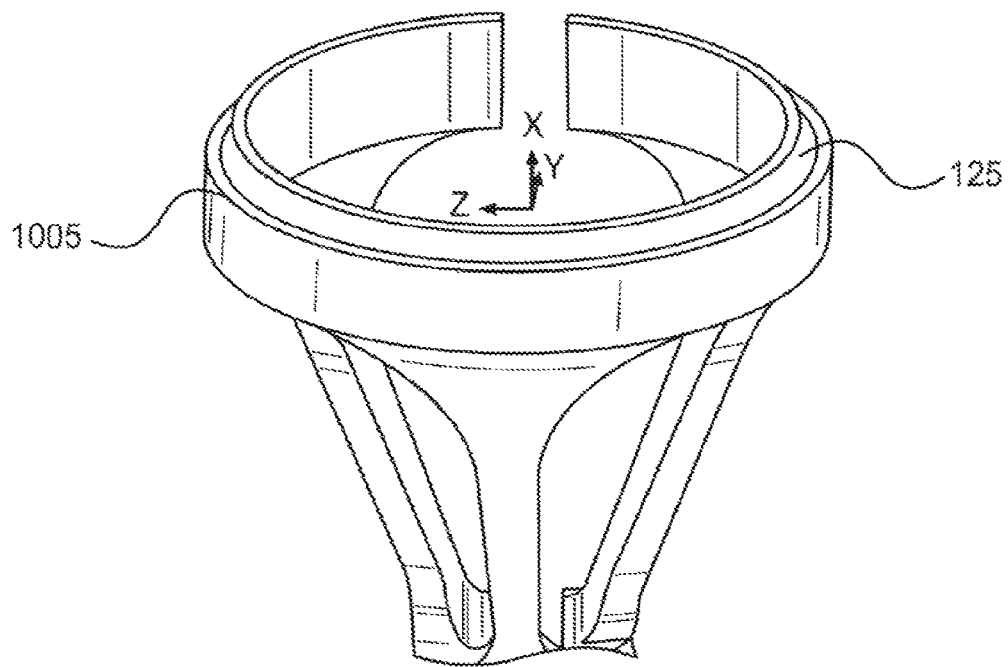
FIG. 10 is an exemplary close-up perspective diagram of the colpotomy ring according to an exemplary embodiment of the present disclosure.
Figure 11:
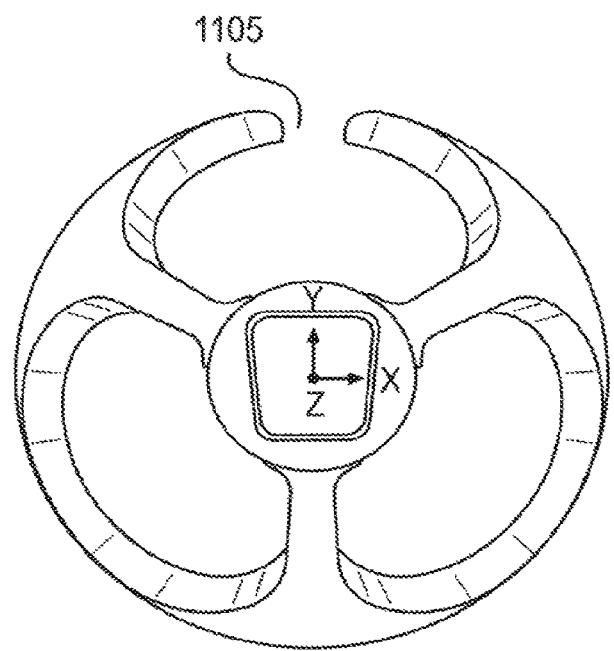
FIG. 11 is an exemplary close-up front view of the colpotomy ring according to an exemplary embodiment of the present disclosure.

As shown in the diagram of FIG. 10, the colpotomy ring 125 can include a ring shelf or a groove 1005 that can facilitate use as a guide for the surgeon when the exemplary device is inserted into the cervix. During use of the exemplary device, for example, the exemplary device can be inserted into the cervix through the vagina, and the surgeon can access the other side of the vagina through an incision in the abdominal wall of the patient. The surgeon can then feel the vaginal wall for the ring shelf or groove 1005 in the colpotomy ring 125, which can serve as a guide from which the surgeon can get tactile feedback about the location of the exemplary device. The surgeon can use this guide to cut the tissue around the cervix. The ring shelf or groove 1005 can also be used as a guide for an electric cutting tool (e.g., to cauterize around the cervix).

In order to facilitate the closing of the exemplary device (e.g., clamping the hook tip of the tenaculum clamp 705 to the variable length tip 120), the colpotomy ring 125 can include a ring slot 1105 that can facilitate the hook tip of the tenaculum clamp 705 to enter through the outer portion of the colpotomy ring 125. (See, e.g., diagram shown FIG. 11). Thus, the colpotomy ring 125 does not block, or otherwise interfere with, the clamping, or scissor action, of the exemplary device. In order to ensure that the ring slot 1105 always substantially lines up with the hook tip of the tenaculum clamp 705, the locking lug 135 can have a structure and/or configuration such that the colpotomy ring 125 can only be placed over the locking lug 135 at a particular orientation (e.g., an orientation that can facilitate the hook tip of the tenaculum clamp 705 to align with the ring slot 1105).

The exemplary device can include a mechanism for which the cup can be placed over the clamp and secured together (e.g., by screwing it in place).

Figure 12:
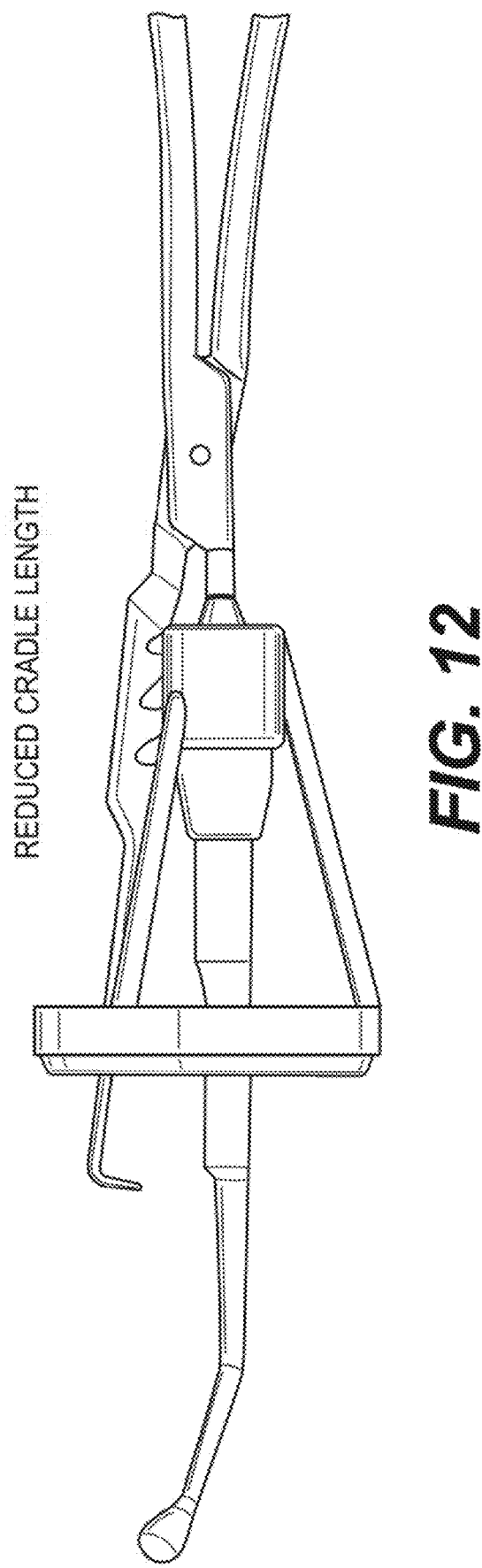
FIG. 12 is an exemplary diagram showing a side view of the exemplary device from FIG. 1 according to an exemplary embodiment of the present disclosure.
Figure 13:
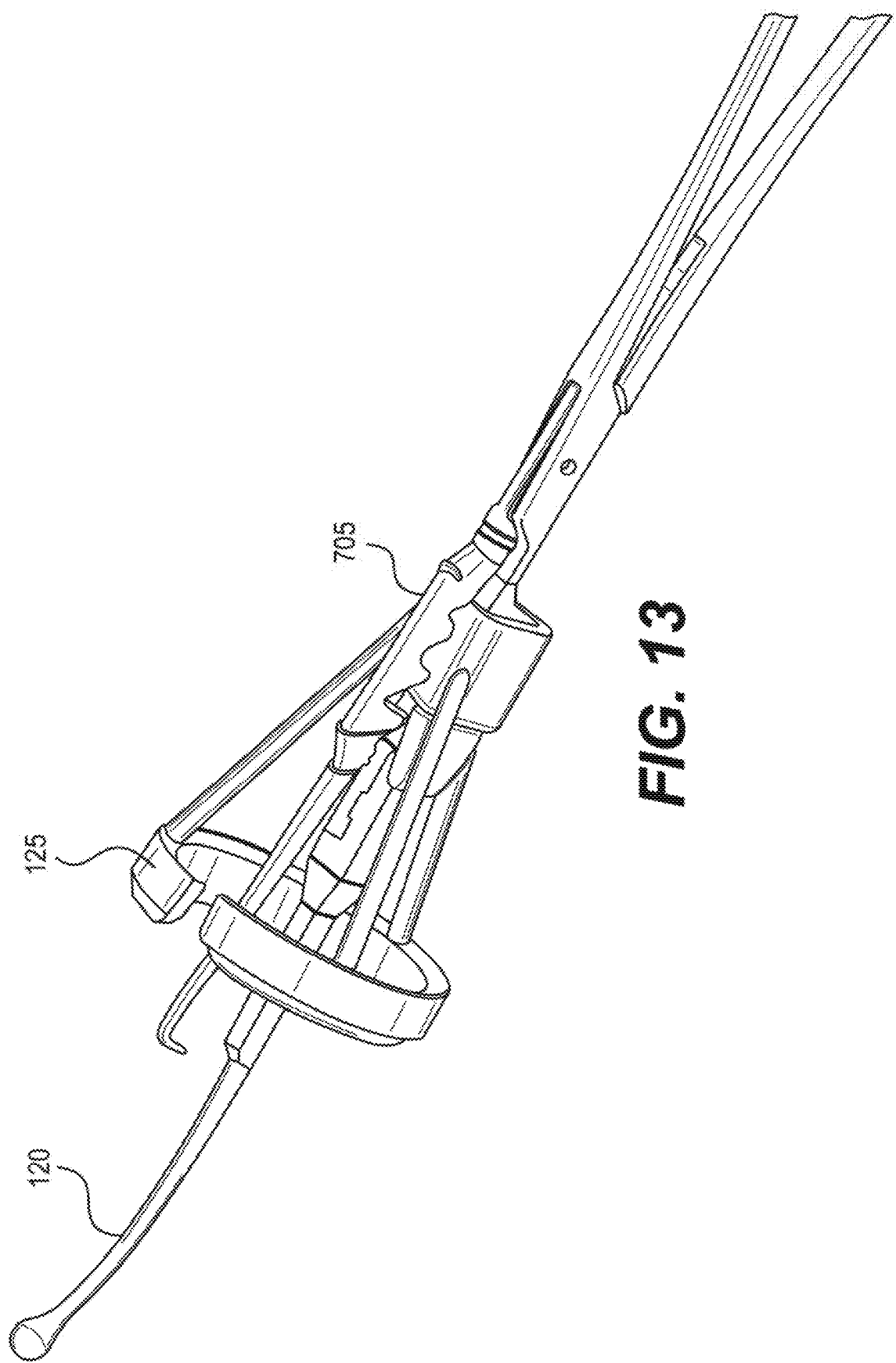
FIG. 13 is an exemplary perspective view of the exemplary device from FIG. 1 according to an exemplary embodiment of the present disclosure.

As shown in the diagrams of FIGS. 12 and 13, the exemplary device can have a reduced cradle length as compared to previous uterine manipulators. A reduced cradle length can reduce the bulk of the colpotomy ring 125 and the exemplary device while still maintaining the functionality and strength compared to other uterine manipulators.

The foregoing merely illustrates the principles of the disclosure. Various modifications and alterations to the described embodiments will be apparent to those skilled in the art in view of the teachings herein. It will thus be appreciated that those skilled in the art will be able to devise numerous systems, arrangements, and procedures which, although not explicitly shown or described herein, embody the principles of the disclosure and can be thus within the spirit and scope of the disclosure. Various different exemplary embodiments can be used together with one another, as well as interchangeably therewith, as should be understood by those having ordinary skill in the art. In addition, certain terms used in the present disclosure, including the specification, drawings and claims thereof, can be used synonymously in certain instances, including, but not limited to, for example, data and information. It should be understood that, while these words, and/or other words that can be synonymous to one another, can be used synonymously herein, that there can be instances when such words can be intended to not be used synonymously. Further, to the extent that the prior art knowledge has not been explicitly incorporated by reference herein above, it is explicitly incorporated herein in its entirety. All publications referenced are incorporated herein by reference in their entireties.

What is claimed is:

1. A uterine manipulator, comprising:
    a clamp arrangement having at least one first tip and at least one second tip, the first and second tips being formed by respective first and second arms, the first and second arms being movable with respect to one another so as to hold tissue therebetween; and
    a colpotomy ring arrangement for surrounding a cervical vaginal junction, the colpotomy ring arrangement including:
        a proximal end configured to be coupled to the clamp arrangement on or at the at least one first tip when the clamp arrangement is provided in an opened position, and
        a distal end including (i) at least one first opening formed by and between an inner surface of a curved ring configuration of the distal end extending along a first plane, and (ii) at least one second opening provided in an outer-most curved surface thereof that extends from an outermost edge of the outer-most curved surface of the distal end toward a center of the at least one first opening, the at least second opening extending along a second plane which is different from the first plane, the at least one second opening being provided for an insertion of the at least one second tip therethrough to enter the at least one first opening when the clamp arrangement is moved into a closed position.

2. The uterine manipulator of claim 1, wherein the clamp arrangement includes at least one of a uterine manipulator or a tenaculum.

3. The uterine manipulator of claim 1, wherein the at least one first tip includes a plurality of removable tips, each of the removable tips having a middle section extending between proximal and distal end sections of the respective removable tip, and wherein the middle section of one of the removable tips has a different length from another one of the middle section of another one of the removable tips.

4. The uterine manipulator of claim 1, wherein the at least one first tip has a middle section extending between proximal and distal end sections of the at least one first tip, and wherein the middle section has a variable length.

5. The uterine manipulator of claim 1, wherein the at least one first tip is removable from the clamp arrangement, and wherein the at least one first tip has a middle section extending between proximal and distal end sections of the at least one first tip, and wherein the middle section has a variable length.

6. The uterine manipulator of claim 1, wherein the at least one first tip is coupled to the clamp arrangement using a key which locks the at least one first tip in place.

7. The uterine manipulator of claim 1, wherein the at least one second tip includes a hook tip.

8. The uterine manipulator of claim 1, wherein the at least one second tip is fixed to the clamp arrangement.

9. The uterine manipulator of claim 1, wherein the at least one second tip extends from a distal end portion thereof for a distance out of an outermost distal edge of the distal end of the colpotomy ring arrangement when the clamp arrangement is provided in the closed position.

10. The uterine manipulator of claim 1, wherein the at least one second tip does not extend out of the colpotomy ring arrangement when the clamp arrangement is provided in the closed position.

11. The uterine manipulator of claim 1, wherein the colpotomy ring arrangement includes at least one of a ring shelf provided on the outer surface thereof or a groove provided on the outer surface thereof.

12. The uterine manipulator of claim 1, wherein the uterine manipulator is configured to be inserted into a vagina of a patient.

13. The uterine manipulator of claim 1, wherein a distance between a first end of the at least one first tip and a second end of the at least one second tip is variable.

14. The uterine manipulator of claim 1, wherein a distance between a first end of the at least one first tip and a second end of the at least one second tip is fixed.

15. The uterine manipulator of claim 1, wherein the colpotomy ring is configured to be coupled to the at least one first tip without being coupled to the at least one second tip when the clamp arrangement is in the opened position.

16. The uterine manipulator of claim 1, wherein:
the at least one second tip includes a hook first portion and a second portion from which the hook first portion extends,
the hook first portion extends a particular distance beyond the distal end of the colpotomy ring arrangement when the clamp arrangement is provided in the closed position; and
the at least one second opening is configured to have the second portion inserted therethrough after entering and passing the at least one first opening.

17. The uterine manipulator of claim 1, wherein the at least one second opening is provided between two opposing ends of the curved ring configuration.

18. The uterine manipulator of claim 1, wherein the opposing ends of the curved ring configuration has a distance therebetween that is unchangeable.

19. The uterine manipulator of claim 1, wherein the curved ring configuration is configured to be immovable when the first and second tips are moved in a directions that is toward or away from one another.

20. A uterine manipulator, comprising:
a clamp arrangement having at least one first tip and at least one second tip, the first and second tips being formed by respective first and second arms, the first and second arms being movable with respect to one another so as to hold tissue therebetween;
a colpotomy ring arrangement for surrounding a cervical vaginal junction, the colpotomy ring arrangement being coupled to the clamp arrangement on or at the at least one first tip, and including at least one opening in an outermost curved surface and extending from an outermost edge of the outer-most curved surface for insertion of the at least one second tip therethrough toward a center of another opening of the colpotomy ring arrangement when the clamp arrangement is in a closed position; and
at least one locking lug configured to be inserted over the at least one first tip in order to secure the at least one first tip to the clamp arrangement, wherein the at least one locking lug is provided away and at a distance from the at least one opening.

21. The uterine manipulator of claim 20, wherein the colpotomy ring arrangement is coupled to the clamp arrangement using the at least one locking lug.

22. A uterine manipulator, comprising:
a clamp arrangement having at least one first tip and at least one second tip, the first and second tips being formed by respective first and second arms, the first and second arms being movable with respect to one another so as to hold tissue therebetween; and
a colpotomy ring arrangement for surrounding a cervical vaginal junction, the colpotomy ring arrangement being coupled to the clamp arrangement on or at the at least one first tip, and including (i) at least one first opening formed by and between an inner surface of a curved ring configuration of the colpotomy ring arrangement extending along a first plane, and (ii) at least one second opening provided in an outer-most curved surface of the curved ring configuration extending from an outer-most-edge of the outer-most curved surface along a second plane which is different from the first plane for insertion of the at least one second tip therethrough toward a center of the at least one first opening when the clamp arrangement is in a closed position,
wherein the at least one second tip extends from a distal end portion thereof for a distance out of an outermost distal edge of the curved ring of the colpotomy ring arrangement and through the at least one first opening when the clamp arrangement is provided in the closed position.

* * * * *